United States Patent [19]

Levine

[11] Patent Number: 4,852,570

[45] Date of Patent: Aug. 1, 1989

[54] COMPARATIVE MEDICAL-PHYSICAL ANALYSIS

[76] Inventor: Alfred B. Levine, P.O. Box 15968, Chevy Chase, Md. 20815

[21] Appl. No.: 308,071

[22] Filed: Feb. 9, 1989

[51] Int. Cl.$^4$ .......................... A61B 5/00; G01D 9/00
[52] U.S. Cl. .................................... 128/630; 128/906; 235/487; 346/33 ME
[58] Field of Search ...................... 235/487, 454, 375; 128/906, 900, 630; 346/33 ME; 364/415

[56] References Cited

U.S. PATENT DOCUMENTS

| | | | |
|---|---|---|---|
| 3,566,365 | 2/1971 | Rawson et al. | 128/906 |
| 3,857,383 | 12/1974 | Sommerfeld et al. | 128/906 |
| 4,033,336 | 7/1977 | Murawski et al. | 346/33 ME |
| 4,422,081 | 12/1983 | Woods | 346/33 ME |
| 4,513,295 | 4/1985 | Jones et al. | 128/630 |
| 4,519,398 | 5/1985 | Lisiecki et al. | 346/33 ME |
| 4,609,812 | 9/1986 | Drexler | 235/487 |

*Primary Examiner*—A. Michael Chambers

[57] ABSTRACT

A medical process and apparatus for repeatedly obtaining short term changes in the physiological functioning of an individual as an aid in diagnosing illness and malfunction, and determining longer term changes and "trends" that are, or may be, indicative of the onset of a developing adverse condition. The process involves repetitive testing of the individual at short term intervals and permanently recording the results of all tests, as well as comprehensive medical data about that individual, in the form of microrecordings on a small, credit card size medical record adapted to be continuously carried by the individual. The extensive compilation of test data and medical data is reviewed and compared at longer term intervals to reveal changes and "trends" in process of development. A similar process is employed for determining changes and "trends" in the degree of physical fitness or conditioning. Apparatus for practicing the processes can include multiphasic diagnostic equipments that perform the numerous tests at frequent intervals, and at lower cost, with reduced need for attending physicians or other medical specialists. The medical history card is intended to be always in the possession and under control of the individual to which it relates, and is always available in the event of an emergency requiring medical assistance.

18 Claims, 1 Drawing Sheet

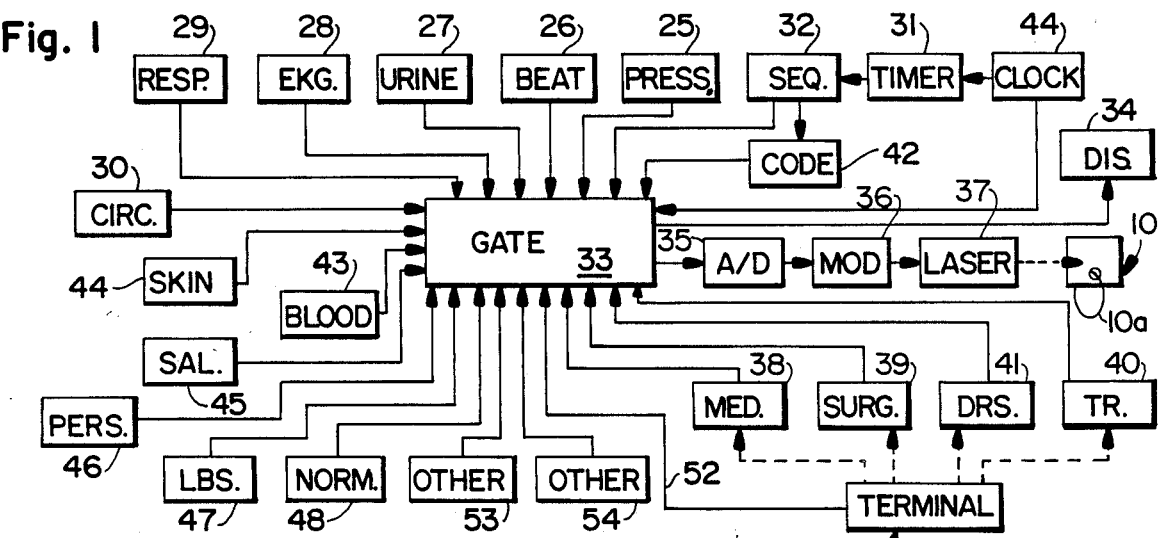
Fig. 1
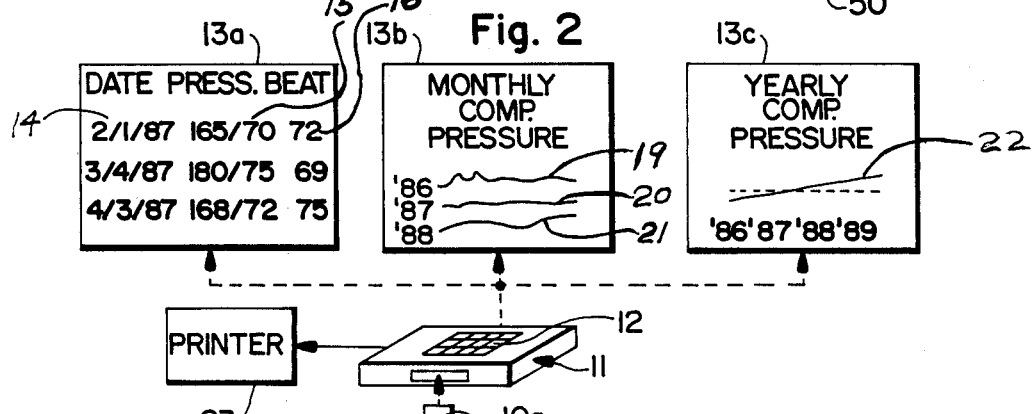
Fig. 2
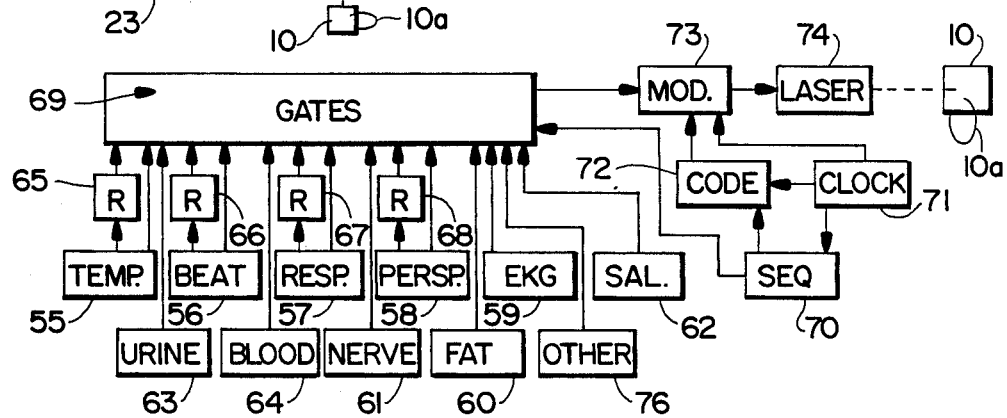
Fig. 3
Fig. 4

COMPARATIVE MEDICAL-PHYSICAL ANALYSIS

STATEMENT OF INVENTION

This invention generally relates to improvements in methods for more accurately diagnosing illnesses of the human or animal by comparing short term changes taking place; and to improvements in the apparatus useful in practising these methods.

BACKGROUND AND REASONS

With the availability of more advanced and precise diagnostic instruments, machines, and systems, medical science can more accurately pinpoint malfunctions and diseases of the body and often apply corrective measures. However, quite often the disease is detected at too late a stage to fully correct the problem, whereas if the developing malfunction had been found earlier, corrective measures may have resulted in a complete cure or at least arresting or neutralizing of the problem.

The reasons for late detection often result from economic inability, neglect, or the unavailability of doctors and needed medical facilities. Although medical authorities recommend periodic medical examinations, the individuals involved often cannot afford the costs of such examinations and testing, and medical insurance policies often do not include the costs of such diagnostic exams and tests unless accompanied by a known specific illness or disorder. Additionally, in an increasingly mobile society, individuals frequently relocate from place to place, and change doctors and other medical services more frequently than in the past. Therefore the doctors often do not have the benefit of long term medical histories of their patients but instead must rely upon limited medical information known by the patients themselves, together with the result of current physical examinations and tests, without the benefit of earlier, more complete medical records pertaining to that individual.

As a result, medical examinations and diagnosis of an individual is often based entirely upon such current information without the benefit of past medical history. Quite often these current measurements and tests only shown results within the so-called normal ranges, that are typical or average of data taken from other individuals, and therefore do not alert the medical examiner to a problem that is in progress but that has not progressed to outside the range of the "average" reading or measurement. On the other hand, if the physician had available a detailed series of past medical tests and findings for comparison, the "trends" or changes in the measured conditions over a long term interval would often alert the diagnostician of a problem in process, or raise suspicions about the onset of a possibly adverse condition that should be more thoroughly checked by further testing. For example, current blood testing might indicate a patient's blood sugar level to be within a so-called normal range, yet comparison of that test with a series of earlier tests of the same individual might reveal a progressive increase in the blood sugar level over the past few years, or other long term interval. This adverse "trend" would then indicate the need for further testing, by such means as a glucose tolerance test, or other, which is not usually given during a routine medical examination. If such further testing confirms the suspicion of onset of a diabetic problem, the physician might then seek to stabilize the patient by change in diet coupled with medication, exercise, and other procedures recommended.

SUMMARY OF INVENTION

To provide a more detailed and informative manner of diagnosing the physiological health of an individual, the present invention provides a method and apparatus for both obtaining and making available in useful form more physiological information about an individual than is usually available. This information includes more frequent tests of the same group of parameters, made under uniform procedures, over a long time period. This permits the physician to more readily observe or detect adverse "trends" that may be indicative of a future problem, so that corrections can be undertaken before a problem becomes incorrectable or irreversible.

More specifically, the method includes periodically taking a comprehensive series of medical tests of an individual at frequent intervals and recording the results of each group of tests in micro form on a small portable, medical history card, that is intended to be carried about on the person of the individual being tested in a continuous manner. The many tests performed in each group are preferably made using automatic, or semi-automatic apparatus without the need for an attending physician or medical specialist, thereby minimizing the economic burden of the more frequent testing procedure. Since the medical history card is intended to be continually carried by the individual, the long term compilation of the many prior groups of tests are always available in the event of emergency or other need of such data.

At regular long term intervals, that may be annually, the individual consults with a physician for an examination. At this time the physician has available for readout and comparison, the cumulative results of the periodically made groups of tests. By comparing like measurements taken of that individual over many spaced periods of time, the doctor can more readily detect changes and "trends" that have progressively taken place over the long term. If such comparisons reveal unexplained, undesirable changes, the doctor is alerted to more intensively investigate the conditions indicated, and take such corrective measures as appear to be necessary.

DESCRIPTION OF THE DRAWINGS

FIG. 1 is a block diagram illustrating an apparatus for micro recording and reading microrecordings of medical test data according to the present invention, FIG. 2 is a schematic illustration showing apparatus for display of medical trend data for analysis according to the invention, FIG. 3 is a block diagram, similar to FIG. 1, and showing apparatus for monitoring and recording physiological data for "trend" analysis of the degree of physical fitness of an individual; and FIG. 4 is a schematic illustration of a visual display screen, similar to FIG. 2, and showing display of the data recorded by the apparatus of FIG. 3.

DETAILED DESCRIPTION OF PREFERRED EMBODIMENTS

Referring to the drawings, and initially to FIG. 1, there is shown one preferred apparatus that may be employed for making the microrecordings on a small card size medical history according to the invention. As shown, the medical history is provided in the form of a small credit card size plastic record 10, that is adapted to be continuously carried about by a user in a pocket or purse, or alternatively provided with a short looped string or strap 10a for enabling the small card to be carried about the neck, underneath the user's clothes, like a military type "dog" tag. This small card 10 contains a great number of lines of micro recording of medical data concerning that user, including the results of frequent groups of physiological tests and related medical information pertaining to that individual. Each different group of such physiological tests is taken at frequent short term intervals, such as every four or six months. Each such group of test may include the results of up to (100) one hundred or more tests, and the small card 10 may have recorded thereon up to ten years (10) or more of such accumulated recordings.

As a result, this small credit card size medical record 10 may contain a comprehensive compilation of frequently made groups of physiological tests and medical information about that individual over a long time period, and this comprehensive medical record is intended to be retained by, and exclusively under the control of that individual. At much longer time intervals, such as every year or two year period, the individual may be examined by a Physician or other medical specialist that supervises the taking of a like number of physiological tests, and compares the current results with those of the many earlier groups that have been recorded on the small card history. Having such a comprehensive medical history of that individual, the Physician can compare the results of many like tests taken periodically over long time periods, and therefore be more able to determine any changes or "trends" that have developed, or are in process of development, that might indicate an adverse condition or one in process of developing. The physician can also compare the many past recordings, or "trends" noted from the many recordings with the so-called normal ranges for all individuals or ranges for selected groups including that individual. This provides the physician or other medical specialist with not only a great deal more medical data about that individual than would normally be available but provides that medical data in a form that can be considerably more useful in analyzing and diagnosing that individual than before.

Returning to FIG. 1, there is shown one preferred apparatus for recording the results of the many groups of tests and related medical information on the small card 10. To provide the great number of lines of medical information on such a small card 10, a very fine light beam, of high intensity, from a laser recorder 37 is used to scan the plastic card 10 in a rectangular raster, and the laser 37 is is electrically modulated at 36 by the signals to be recorded to permanently record the medical data along each very fine line in sequence. Also recorded on the card next to the recording of each different test or other medical data is an "address" or coding, generated by a coder circuit, to identify each such test result or other medical information, and still further the date and time-of-day signal of that test is recorded from a clock 44, to provide the date and time of that particular test or entry of other information. These various medical test signals, address codes, and date and time signals may be recorded by the modulated laser 37 in digital form, or other, as is now conventional in compact disc recording of audio and/or video signals.

FIG. 1 also illustrates the many different kinds of physiological test results that can be recorded in each of the frequent groups of medical tests made of that individual and recorded on the card. As shown, in conventional fashion the individual is monitored by many different transducers to read the conventional body functions including blood pressure 25; heart beat 26; respiration 29; urine analysis 27; blood circulation 30; blood composition (eg chlorestorol etc.) 43; skin color 44; saliva 45; perspiration count 46; EKG 28; and many others. Each such function is monitored by a transducer, or entered by a keyboard-terminal 50 into the gating system 33 of the recorder. Transducers with amplifiers for monitoring all of these physiological functions and conditions are well known, and available on the open market to physicians and other medical personnel. Many of such transducers generate electrical signals including EKG, temperature, blood pressure, and many others, and are therefore directly connectable to the laser recorder, with or without suitable amplification. Other sensors detect and measure other body conditions and functions using various radiation, including infra-red, ultraviolet, sonic and ultrasonic waves, magnetic fields, NMR, and a number of variations. As well known, these sensors are usually provided with electrical transducers for generating the electrical signal useful in the microrecording according to the present invention. Since these tests and many others are presently available, a further description thereof is not necessary to an understanding of the present invention, for those skilled in the art.

In addition, it is desired to record at these frequent short term interval tests other medical information concerning that individual, including any medication in use 38; any surgery performed 39 since the last recorded tests; and the name and addresses of all physicians and other medical specialists 41 that have treated that individual. All of this information is entered into the microrecorder using the keyboard-terminal 50.

Still further, for each such group of tests made at short term intervals, the individual is preferably interrogated for additional information concerning medical information and physiological and mental condition, and the response are entered into the microrecorder at 52 using the keyboard-terminal 50. For example, the individual is interrogated concerning eating and sleeping habits, smoking, alcohol and drug consumption, bowel movements, and many other aspects indicating the state of physical health, and the answers are entered into the microrecorder for recording on the small plastic medical history card 10. With each such answer is also recorded an identification address and the date and time, all as discussed above.

Returning to FIG. 1, each of the electrical signals for the various large number of tests in each group, and for the other information discussed above, is directed to the gating system 33, for enabling the sequential recording of these signals on the card history 10. The gating circuits 33 are controlled by a timer circuit 31 and sequencer circuit 32 (eg shift register, as well known in the art), to sequentially gate each of the electrical signals, and associated address signals and time-date signals to the modulator 36 that controls the recording modulation of the laser 37.

In the event that the various signals are not generated in digital form, the output of the gating circuits 33 is directed to an analog to digital converter 35, to digitize these signals for recording. Alternatively, in the event that the outputs of the various transducers are in digital form, the design of the gating circuits is appropriately changed and the analog to digital converter circuit 35 is not required.

In FIG. 1, as the small plastic card 10 is being recorded with the various medical data after each short term group of tests, it is desired that the medical information being recorded is concurrently displayed on the screen 34 of a cathode ray terminal or the like. This enables the detection of any errors in the recorded information. Where any error has been detected, the keyboard-terminal 50 may be used to stop the recording of data at that point, and permit an error code to be entered on the medical card 10, following the erroneous recorded entry. That entry can then be corrected using the terminal 50, and the corrected signal can be recorded on the medical history card 10.

In a preferred system, the complete monitoring and recording system shown in FIG. 1 is preferably a completely automated system, for testing and recording the results on the card 10, without the need for an attending Physician or Medical specialist, thereby to reduce the costs of making the many periodic groups of tests made at short term intervening intervals. Many of the standardized testing equipments are now available permitting individuals to make their own tests of blood pressure, heart beat, weight, height, respiration, and many others. Alternatively nursing aids or less specialized technicians can be employed to perform such frequent testing, using available automatic and semi-automatic monitoring and recording apparatus, to reduce such costs. At present, there is available completely automatic and semiautomatic equipments for performing most of the many tests indicated in FIG. 1, and others, and it is expected that self contained medical testing booths will soon be made available to the public, in the form of unattended, coin operated testing booths for performing multiple physiological tests and providing a print-out of such multiple medical tests.

FIG. 2 schematically illustrates the manner in which the comprehensive groups of recorded tests may be used by a Physician or trained medical specialist for "trend" analysis or diagnosis of an individual to determine an adverse medical condition, or a developing adverse condition.

As shown, the Physician is provided with a microcard reader 11 and keyboard selection terminal 12 for reading the microrecordings from the small card 10; and for selecting from the card 10 any like series of medical test results for comparison and "trend" analysis. As shown, the Physician's terminal includes a large visual display screen coupled to the terminal 11 for displaying the selected test data together with a printer 23 for printing a copy of the information displayed on the screen 13. As shown by the first display 13a on the screen 13, the Physician can select from the card 10 the results of a number of like medical tests and display these results in tabulated form for comparison. The first vertical column 14 on the screen 13 shows the different date of each test, such as "2/1/87", "3/4/87" and so forth. The second vertical column identifies a first one of the medical tests being performed at the different dates, such as "blood pressure" readings 15. The next vertical volumns 16, 17, and 18, and so forth, list the results of other of the medical tests performed at the different dates including the "heart beat rates" in column 16; the "urine analysis" in column 17; and "EKG" waveforms in column 18.

These test results for each different kind of medical test, made on each of the different dates, are conveniently tabulated in the display 13a, each beneath the other, whereby the physical or medical specialist can readily determine the changes or "trends" that have taken place over the different short term intervals. Since each different one of the many test results is identified on the card 10 by both a type code and by the date of the test, the Physician can selectively read out of the card 10, the results of any series of like tests for such comparison and "trend" analysis.

Where it is desired to graphically display the changes in any like series of test results, over any desired period of time, the changes in any measured medical function can be graphically plotted by the terminal 11 and display 13 as shown by the alternative display at 13b. As illustrated at 13b, the changes in the "blood pressure" readings for the three years of 1986, 1987, and 1988 are depicted on the screen 13 after read-out of the many test results from the medical history card 10. As shown, the upper curve 19 showns the changes taking place during the year 1986 for that individual, taken from the number of test results recorded on the card 10 during that year. The next curve 20, below curve 19, shows the variations in that individual's blood pressure readings during the next year 1987; and the third curve 21 plots the same type of information for the following year 1988. These three curves 19, 20, and 21 therefore graphically illustrate in a convenient fashion any changes occuring in that measured function during the three years being displayed, and enable the physician or other specialist to note any marked changes or "trends" that may be indicative of an adverse medical condition or one in process of development.

In a similar manner, any one or more of the many other different types of medical tests recorded on the card 10 may be selectively read-out and displayed eith in tabulated form, as shown by the display 13a, or in graphical form as shown by the display 13b. Where the multiple groups of medical tests have been accumulated on the small card 10 for a number of years, it may also be desired to graphically display the changes or "trends" in any measured function over the multiple yearly period, as depicted in the display 13c on the screen 13. Here the graphical plot of "blood pressure" readings shows the changes occuring over the three year period of 1986 to 1988, inclusive. This plot 22 is obtained by the terminal 11 averaging the group of blood pressure readings from the card 10 for each year and graphing such average s as the curve 22 for the three year period.

Many other ways of comparing the medical test results from the many like readings of each different function can be performed using conventional computers or terminals 11. For example, each later test result can be subtracted from the one earlier, and the differences plotted or graphed on the screen 13 to display the variations. Any unusual or marked difference could be indicative of a malfunction, or one in process, resulting in that physician making further tests or inquiries. Similarly, the differnet medical test results can be ratioed, added, averaged, or statistically combined, or otherwise mathematically processed to reveal changes or "trends" that might be meaningful of an adverse condition or one in development. Desk top computers and terminals for performing these and many other programmable functions, are presently available on the open market and a further description of such known apparatus is not believed to be necessary for those skilled in the art.

A great deal of so-called "normal range" medical data has been compiled in the past, and is presently being added to, setting forth the normal ranges of results of medical test data for individuals and subgroups of individuals. At present, most physicians rely upon comparing the medical test results from their patients with such "normal" ranges of readings, to detect any adverse conditions. However, the present invention differs from this standard or conventional practice by looking at and comparing the results of many tests of the same individual to determine the extent of changes, and detect "trends" that might be indicative of an adverse condition or the onset of such an adverse condition. Of couse, the test results for any individual would also be compared with the so-called norms or normal ranges, for that person or subgrouping, as an additional reference standard or basis for comparison, just as the physician would use other information about the patient, such as hereditary and environmental conditions as a further aid in diagnosis of malfunction.

Briefly recapitulating the steps of the preferred method as thus far described, each person is initially furnished with a small pocket size, portable card 10 for storing a very comprehensive medical history in the form of many laser inscribed microrecordings on the card 10. This small card 10 is intended to be continuously carried on the person of the individual, so that the recorded medical history is always available in the event of an emergency. The many microrecordings on the card 10 contain the test results of medical tests and related medical information about that individual taken at frequent short term intervals. Each such group of tests include the many conventional medical tests as well as many others, and each different kind of test result is identified on the card 10 by a recording of a code alongside that result together with a recording of the date and time of the test.

Also recorded on the card 10 at each interval is an update of physical and medical information about that individual, including weight, all medical operations and procedures since the last recorded entry and all medications in use and the amounts, as well as all illnesses. Standardized information about that individual is recorded earlier, including height, blood type, birth date, color of eyes and hairs, all hereditary diseases and factors, as well as any other medical information that might be noted by a careful and thorough Physician.

Still further, at the time of taking and recording the results of the frequent medical tests, the individual is interrogated about many matters of health, including eating and sleeping habits, consumption of tobacco and alcohol, use of drugs, and others, and the answers are recorded on the card along with the identifying codes and the date and time of the interrogations, as discussed above. As a result, the card 10 contains a very comprehensive collection of medical information about that individual, that has been updated at frequent short term intervals.

At periodic long term intervals that may be up to every year, or longer, it is intended that that individual consult with a physician or other medical specialist, for an annual examination, or the like, that includes the taking of a like series of medical tests, and the collection of updated medical information of the same types gathered in the many past tests and interrogations taken at short term intervals. Using the recordings on the portable history card 10, the physician compares the results of each of the medical tests with the many taken earlier, to determine any changes and "trends" that might indicate an adverse medical condition or one in progress. Since all of the recorded test results or other data has been identified by an address code and by the date and time of entry, the physician can readily select from the card 10 any desired data for analysis, comparison, and "trend" analysis. Since the physician also usually has available information concerning the so-called "normal" ranges of test results for groups of other individuals that are similarly situated, the "trend" or deviations for that individual can also be compared with the "normal" ranges as a further aid in diagnosing any adverse medical condition or an approaching onset of such condition.

Since any ones of the recorded test results and data can be selectively called up from the card 10 by the Physician, the individual readings or test results can be variously mathematically processed to obtain differences, percentage changes, ratios, average readings, and others to assist in "trend" analysis of the medical condition of that individual. The various, frequently made, short term interval test results obtained from the card 10 can also be plotted or graphed on a computer terminal available to the Physician, to more readily detect both long and short term changes in any measured condition of that individual.

Where the individual has made use of this process for a period of time, eg a few or more years, the compilation of useful medical information on the card 10 about that individual becomes quite extensive and far greater than is usually available to a physician when conducting a medical examination of a patient. Furthermore, the medical history 10 can be made available to any physician or specialist by that individual, whereby the individual can change locations, and for other reason use other medical persons, with complete assurance that the new physician or medical specialist has complete medical data and history available for diagnosis and trend analysis. If continuously maintained on a regular basis, the card 10 may conceivably contain a complete birth to death medical history for that individual.

To minimize the costs of the frequent medical testing at short term intervals, it is preferred that the tests be conducted by an automatic or semi-automatic multiphasic apparatus without the need for an attending Physician or other medical specialist. One such multiphasic medical testing facility is disclosed in U.S. Pat. No. 3,566,365 of the Serle Medidata Inc. As discussed above, such facility also preferably includes an interactive interrogation system for obtaining updated medical information from the individual, and such a system is disclosed by Searle Medidata Inc. in its U.S. Pat. No. 3,566,370. Another semiautomatic system of this type is provided by the Medical Scientific Information Corporation of Florida, and is disclosed in its U.S. Pat. No. 4,033,336. Systems of this type materially reduce the costs and time involved in making the frequent medical tests, at short term intervals; and are also more convenient to use than having such many routine type tests performed at the office of a physician or other medical practicioner. Such unattended multiphasic medical testing stations can be provided at many different convenient locations, and be available without the need for appointments in advance. Such facilities can also be provided in the form of self-contained units or rooms, using unattended coin operated or credit card operated means of payment. In such event, a user need only insert a credit card for debiting the charges involved, and insert his small portable medical history card 10 in the slot of a laser printer that is provided for receiving the microrecordings of the test results. Instructions for informing the individual regarding the simplified procedures to be followed in having the tests performed are displayed on the visual screen of terminal or printed, as disclosed in the above patents. An updated medical history of that individual is obtained by displaying the questions on the visual screen, and having the individual respond thereto using a keyboard terminal, as also disclosed.

As known to those skilled in the art, other types of apparatus may be employed in practising the processes of the present invention. For example, electron beam recorders may be used instead of laser recorders, for permanently recording the microrecordings of test data on the plastic card 10. Similarly, available ionic recorders, or photographic types using very fine light beams may be used, as well as others. However, at present laser recorders have been well developed and are now extensively in use for compact disc recording of audio and video information, and such recorders are therefore preferred for making the microrecordings for that reason.

As generally described above, in a preferred process and system, an address or identity code is recorded in micro size form on the card along with the result of each test for enabling the results of a past series of any group of like test results to be selectively retrieved from the card 10 for comparison and "trend" analysis. Thus for example, all blood pressure tests results would be identified by the same code, along with the different date and test that each such test was made. Alternatively, other available techniques may be used for selectively retrieving from the card 10 the results of many earlier like tests for comparison. For example, the small card 10 can be subdivided into a number of different spatial sections (not shown), and all tests of a similar kind can be recorded in a common section on the card 10 along with the date and time that each test was conducted. The series of related test results can then be read out of the card 10 in tabulated form for display on the screen, as generally discussed above.

To prevent any misuse or unauthorized use of the medical information recorded on the card 10, this data may be recorded in a coded form (not shown) that can be read out and decoded only with entry of a secret decoding number available only to the person whose data is recorded on the card 10. Where a user consents to the reading of the card the owner inserts this secret decoding number into the keyboard 12 of the card reader 11, enabling the reader to read out and decode the medical data for display on the visual display screen 13, as discussed above in FIG. 2. Other known methods and apparatus are presently available to prevent unauthorized disclosure of the medical information that has been microrecorded on the card 10, as is known to those skilled in the art.

FITNESS AND TREND ANALYSIS

An alternative process and apparatus of the present application is a determination of the level or degree of physical fitness or conditioning of an individual, and the determination of changes or "trends" in such condition. In this alternative process, a group or series of like tests are taken of an individual at frequent short term intervals, and the results of such tests are microrecorded on the small card 10 for later comparison and "trend" analysis. However, unlike the physiological tests used for medical diagnosis of health or illness, the tests for physical fitness are instead primarily intended for determining the degree of physical conditioning and efficiency of the body to exercise, as well as its degree of response and reflexes to various external stimuli.

At periodic intervals that may be after the completion of each such group of fitness tests, the recorded test results for like functions are individually compared with those obtained in the earlier series of tests to determine deviations, changes, and "trends" from the measured functions. The test results are also variously mathematically processed and compared, and/or graphed or plotted over various longer time intervals to show the changes and "trends".

FIG. 3 illustrates one apparatus that may be used in the practice of this "trend" analysis process according to the present invention. As shown, a large number of transducers are provided to detect various body functions, including temperature 55, heart beat 56, respiration rate and volume 57, perspiration and rate 58, EKG 59, fat-muscle ratio 60, nervous response 61, saliva content 62, urine analysis 64, blood analysis 64, and many others. Rate circuits 65, 66, and 67 are also coupled to the transducers for temperature 55, heart beat 56, respiration 57, and perspiration 58, respectively, and to others, to determine the rate of changes of these measured conditions.

All of these transduced signals are directed to a gating system 69, that, in turn, is controlled by a sequencing circuit 70, that may comprise a shift register circuit. The gate system 69 and sequencer 70 function to sequentually sample each of the transduced signals in order, and direct the sampled signals to a modulator 73 for modulating the light emissions of a laser beam recorder 74. The sequencer circuit 70 is controlled by a constant frequency clock and timer circuit 71, to selectively turn on and off the gates for each of the transduced body signals, in a regular sequence, thereby to direct each such signal in turn to the modulator 73.

In the same manner as discussed above, the laser 74 is modulated to record each of these sampled signals in turn on the small plastic card 10, in the form as a series of microrecording thereon. A code generator circuit 72 is also energized by the clock-timer circuit 71 to sequentially generate a different code for each different one of the transduced body signals, and in sycronism with the controlling of the gating system 69, and these different codes are directed to energize the modulator 73 after each associated transduced body signal is gated by the gating system 69. As a result each one of the transduced physiological or body function signals is sequentially recorded on the card 10 along with a code identifying that function, such as heart beat etc., and with the date and time of day for that test also being recorded on the card 10.

In a preferred process, the individual is subjected to a fixed program of exercising activities and the series of transducers monitors the various body functions during such fixed exercise program. This same fixed exercise program is regularly repeated at frequent short term intervals, such as monthly, and the results of each such group of tests made during each such exercise program are recorded on the card 10 as the exercise program is being performed. For example, one such exercise program covering an interval of 60 minutes, may include a first segment or period of 10 minutes at rest; followed by an accelerating level of programmed exercise for the next 15 minutes; followed by a continuation of the exercise at a constant intensity for the next 10 minutes; followed by a decreasing level of the programmed exercise for another 15 minutes to a rest condition; and finalized by an ending rest period of 10 minutes. During each such segment of this fixed exercise regime, the various physiological signals from the transducers are successively sampled and recorded on the card 10, with the proper identifying code for each signal, and with the date and different time-of-day for each sampling of the signals during that test.

FIG. 4 illustrates one of the many groups of sampled signals recorded during each exercise program. As shown, the date 82 for that exercise program is recorded as "8/15/87". On the lowermost line is recorded the time-of-day 77 for each sampling of the signals during that exercise test, including the times "8:02", "8:04" and the like, as shown. Above each of said time-of-day instants, there is recorded, in vertical tabulated arrangement, the body signals that are sampled and recorded at that instant, including in the next line above, the heart beat rate 78, the body temperature 79, the respiration 80, and the blood pressure 81, all as shown. The signals recorded at the first time instant of "8:02", therefore comprise a heart beat signal of "68"; a temperature signal of "98.5"; a respiration signal of "2"; and a blood pressure signal of "140/60". In a similar manner all of the other transduced body signals, shown in FIG. 3, as well as still additional ones, are recorded on the small card 10, in vertical tabulation above the time-of-day of "8:02". Each such recorded signal is followed by a recording of a different address code (not shown) that identifies the previous recording as being for "heart beat rate" or other function, as described above.

On the next vertical column on the card 10, the same group of body signals are recorded in corresponding vertical tabulated arrangement, but showing those readings or changing values that are sampled at the next instant time-of-day of "8:04" in the fixed program of exercise. In like manner, each succeeding vertical column of recorded numbers, shows the sampled body signals at a different time instant in the above described program of exercise.

This fixed program of exercise is designed to variably stress that individual in a controlled manner and to measure and record the body responses and function under the fixed program of different conditions. To obtain reliable information and data for comparison and "trend" analysis, this fixed exercise program is duplicated as closely as possible, for the next exercise test to be taken the following month, and each subsequent month, or other relatively short term periods thereafter. To reproduce the same exercise regime for at each of the spaced apart time intervals, accurately controllable exercising appliances are preferably used, such as powered treadmills (not shown), powered stationary bicycles (not shown) or others. Each of these appliances is controlled in a time variable manner, by a controller, to duplicate the same fixed program of exercise each month, or other short time interval selected. As a result the individual is periodically subjected to the same fixed program of exercising activities, and during each such program, the many body activities and functions are detected and sampled at spaced time instants, and recorded on the small card 10. Thus the identical exercise program is repeated at short intervals, and the same group of body functions and responses are measured and recorded on the card 10 at the same time instants during each program. As will be appreciated by those skilled in the art, the very fine coherant beam provided by the laser 74 enables a great number of microrecordings to be recorded on a small plastic card 10, and therefore the repeated monthly test data for a number of years can be readily recorded on the same card 10. Accordingly it will be understood, that FIG. 4 showing the recordings for only one such exercise test occupying almost the entire surface of the card 10, is for purposes of illustration only and is not intended to be a showing of actual space requirements for the recorded information.

At periodic long term intervals, the microrecordings on the card 10 are read out and the results of like functions are compared for "trend" analysis of changes in physical fitness. Thus for example, the heart beat rate recordings 78 for that individual while at rest can be compared with the same recordings for many earlier months, or may be plotted similarly to that of FIG. 2 to show any changes or improvements. It is well known that as physical fitness improves, the cardiovascular system is strengthened and becomes more efficient, slowing the heart beat while more efficiently pumping the flow of blood. Improvements in the degree of physical conditioning or fitness are therefore readily shown by the "trend" comparison process. In a similar manner, at any given segment of the fixed exercize regime, any given test function can be compared with the same function recorded in a series of earlier tests to determine the changes and improvements, if any, in the conditioning or fitness of that individual. Since a considerable number of body functions are transduced and compared with earlier results according to the present invention, as generally illustrated in FIG. 3, the degree of physical fitness and changes therein with time can be determined with a precision heretofore unobtainable.

ADDITIONS

It will be appreciated by those skilled in the art of medical diagnosis, that the above process for determining changes and "trends" in physical fitness, is also useful for medical "stress" testing. In conventional practice, medical "stress" testing also involves monitoring body functions before, during, and after an exercise regime. However, unlike the present invention, the monitored test results are compared with so-called "normal" ranges of test results obtained from groups of other individuals that are similarly situated (eg same age group, same sex, etc.). According to the present invention this process differs from that conventionally followed by comparing the test results with those obtained from the same individual in a series of earlier tests that have been repeatedly performed at short term intervals. Having the results of many earlier tests taken under similar conditions, any adverse changes or "trends" can be readily noted.

In recent years, medical science has rapidly introduced a number of additional improved types of body monitors and sensors for measuring various physiological functions, and it is expected that still further advances in such diagnostic instruments will be made in the future. For example, present medical analysis of body fluids including blood, urine, saliva, perspiration, ear wax, glandular secretions, biopsy samples, and others, rely upon rather slow and inconvenient methods of chemical processing or organic changes, sometimes coupled with other forms of optical or other read out analysis. These test methods are being rapidly replaced by more prompt and convenient methods including electronic devices, electo-optical techniques, microwave testing, sonic and ultrasonic sensors, and others. Many of these newer processes and techniques can be performed by semi-automatic or automatic instruments without the need for physicians, technicians, or other specialists in attendance, and are therefore useful in the practice of the processes of the present invention where frequent series of tests are to be made at short term intervals. Additionally, new sensors are now available, and more will be made available in the futre, for testing other physiological functions of the body that have not been previously tested. For example, body tissue composition, distribution of fat to muscle, bone density and brittleness, skin texture, composition, and resiliency, hair composition and growth, hair root structure, efficiency of the body in generating various protective secretions including eye tears, ear wax, perspiration, and others. Changes in the internal content and fuctioning of tissue, glands, bones, hair, teeth, skin, and other tissues and organs, will be more readily detected, to permit determination of the rate of aging, and changes therein due to stress and illness. It will be therefore appreciated that the processes of the present invention are not limited to the use of presently available sensors and transducers for performing conventional diagnostic measurements but that others will become available for use in these processes to great advantage in determining changes and "trends" in various physiological functioning, and in physical fitness.

Where it is desired to perform the processes of the present invention using portable apparatus that is adapted to be carried about by the individual while detecting the various body functions, conditions, and compositions, this can be performed by using apparatus similar to that shown in FIGS. 1 and 3, but coupling the modulators 36 and 73, respectively, to a portable tape recorder or the like (not shown). The temporary recording of test results on a magnetic tape or other can later be transferred to the plastic card 10 for permanent microrecording of the test data as described above. Alternatively, portable laser recorders are now available for playback of audio information from compact discs, and similar portable recorders may carried about by an individual for recording the medical data on a small plastic card 10.

Although the present application discloses only certain preferred apparatus and processes for practising the invention, it will be understood by those skilled in the art that many changes may be made without departing from the spirit and scope of the invention. Accordingly, this invention is to be considered as being limited only by the following claims:

What is claimed is:

1. A method for comparative trend medical analysis of persons comprising the steps of:
    a. repetitively performing a multiphasic medical examination of said person at frequent short term intervals less than one year,
    b. each of said multiphasic medical examinations comprising the step of examining and monitoring a like series of different physiological conditions during each short term interval,
    c. each of said repetitive multiphasic examinations comprising the additional step of recording each one of said different monitored physiological conditions onto a miniature medical record adapted to be retained by that person,
    d. recording on said miniature medical record along with each of said different multiphasic medical examinations the date that such examination was performed,
    e. recording on said miniature medical record along with each one of the monitored physiological conditions a unique identification of that type of physiological condition,
    f. whereby after passage of a long term interval comprising a plurality of short term intervals, said miniature medical record contains a plurality of chronologically related recordings for each different type of monitored physiological condition, with each one of the different recordings being uniquely identified on the record by the type of condition being monitored and by the date of the measurement,
    g. at long term intervals after the passage of plural ones of such multiphasic examinations, selectively retrieving from said miniature medical record a chronologically related series of recordings for one of the different physiological conditions being monitored,
    h. comparing the individual recordings of said related series of like conditions being monitored with each other to chronologically detect any unusual trends or changes in that monitored condition occuring over that long term interval,
    i. at long term intervals after the passage of plural multiphasic physiological medical examinations, selectively retrieving from said miniature medical record, a second series of chronologically related recordings for a different monitored physiological condition,
    j. comparing the individual recordings of the retrieved second series of recordings with each other to chronologically detect any unusual trends or changes in the different monitored condition occuring over that long term period,
    k. and cumulatively repeating the same multiphasic medical examination of that person over additional short term intervals, and cumulatively recording all of the like monitored conditions for each such examination on said miniature medical record, together with the date of each said examination and a unique identification of each type of monitored physiological condition,
    l. whereby said miniature medical record retained by the person retains a progressively lengthened series of chronologically made recordings for each different monitored physiological condition, with the passage of time, and accordingly provides a progressively greater base for comparative trend medical analysis of that person.

2. In the method of claim 1, the additional step of:
    m. at long term intervals, comparing the retrieved recordings from the miniature medical record with a normal range for that condition to detect any unusual changes or trends from the normal ranges.

3. In the method of claim 1,
    the step of recording a unique identification of each different recorded condition comprising the recording of a unique digital code for each different physiological condition that is chronologically monitored.

4. In the method of claim 1, the step of recording a unique identification for each different recorded condition comprising the recording of all like physiological conditions adjacent one another at a given spatial location on the miniature medical record.

5. In the method of claim 1,
the step of retrieving and comparing the recordings of like physiological conditions being progressively monitored at short term intervals including the additional step of:
m. mathematically processing the series of progressively recorded related recordings and displaying the mathematically processed recordings.

6. In the method of claim 5,
the step of mathematically processing the series of retrieved recordings comprising the step of averaging said recordings.

7. In the method of claim 1,
the step of retrieving and comparing the recordings of like monitored conditions including the step of:
m. displaying the chronologically related recordings as a variable with time.

8. In the method of claim 1,
the step of retrieving and comparing the recordings of like monitored conditions including averaging said retrieved recordings.

9. In the method of claim 1,
the step of retrieving and comparing the recordings of like monitored conditions comprising:
m. mathematically processing said retrieved recordings to derive one of the differences between recordings; the ratio of different ones of the recordings; and the average of a series of such recordings.

10. A method for comparative trend analysis of a person comprising the steps of:
a. repetitively subjecting the person to the same fixed program of physical activity at short term intervals less than one year,
b. at each such program performing a multiphasic examination of that person,
c. each said examination comprising the step of monitoring that person for a series of different physiological conditions,
d. each of said examinations comprising the additional step of recording each one of the different monitored physiological conditions onto a miniature record adapted to be retained by that person,
e. recording on said miniature record along with each of said different multiphasic examinations the date that such examination was performed,
f. recording on said miniature record along with each different monitored condition a unique identification of that type of physiological condition,
g. at long term intervals following the passage of plural ones of such multiphasic examinations, selectively retrieving from said miniature record a chronologically related series of recordings for one of the different physiological conditions being monitored,
h. comparing with each other the individual recordings of the series of like conditions being monitored to detect by such comparisons any unusual trends or changes in the monitored physiological condition occuring over that long term interval,
i. at long term intervals following the passage of plural ones of such multiphasic examinations, selectively retrieving from said miniature record, a second series of chronologically related recordings for a different monitored condition,
j. comparing the individual recordings of the retrieved second series to chronologically detect any unusual trends or changes in the different monitored condition occuring over that long term interval,
k. whereby said miniature record contains a progressively lengthening series of chronologically made recordings for each of the different monitored conditions, with the passage of time, and accordingly provides a progressively greater base for comparative trend analysis of that person.

11. In the method of claim 10,
the step of recording each different monitored physiological condition being accompanied by recording a different unique digital code to identify the type of condition being monitored.

12. In the method of claim 10,
the step of comparing the rerieved individual recordings including the additional step of:
l. comparing the retrieved recodings with a normal range for that monitored condition.

13. In the method of claim 10,
the step of retrieving and comparing the recordings of like physiological conditions at long term intervals including the additional step of:
l. mathematically processing the retrieved recordings and displaying the mathematically processed recordings.

14. In the method of claim 10,
the step of retrieving and comparing the recordings of like physiological conditions at long term intervals comprising the steps of:
l. mathematically processing the retrieved recorded conditions to derive one of the average of a series of such retrieved recordings; the ratio of different pairs of such recordings; and the averages of sleected groups of said recordings,
m. and displaying the mathematically processed retrieved conditions as a variable parameter with time.

15. A method for comparative trend analysis of a person comprising the steps of:
a. repetitively performing a multiphasic physiological examination of said person at frequent short term intervals less than one year,
b. each of said examinations comprising the steps of monitoring the same plurality of different physiological conditions in a comparable environment,
c. at each examination, recording the results of each of the plurality of different monitored physiological conditions in the form of microrecordings on a miniature record,
d. said recording steps additionally including the step of recording the data for each such multiphasic examination on said record,
e. said recording steps additionally including the recording of each different monitored condition at a different address on the miniature record,
f. at long term intervals following a plurality of short term intervals and multiphasic examinations, selectively retrieving from the miniature record a chronologically related series of recordings for one given type of monitored physiological condition,
g. comparing the retrieved recordings for said given type of physiological condition to detect any unusual trends or changes in the monitored condition occuring over the long term interval, h. at said long term intervals after the recording of plural ones of the results of said multiphasic examinations, selectively retrieving from the record, a second series of chronologically related series of recordings for a different type of physiological condition being monitored, i. comparing the retrieved recordings for the different type of physiological condition with each other to detect any unusual trends or changes in the monitored condition occuring over that long term interval, j. and repeating the above mentioned steps of retrieving and comparing the retrieved recordings at successive long term intervals following successive series of multiphasic examination.

16. In the method of comparative analysis of claim 15, the additional step of subjecting the person to the same fixed program of physical activity in conjunction with each of the multiphasic examinations.

17. In the method of claim 15, the additional step of:

k. at said long term intervals, mathematically processing the retrieved recordings, and displaying the mathematically processed recordings.

18. In the method of claim 15, the step of comparing the retrieved recordings being performed by displaying the retrieved recordings as a varying parameter with time.

* * * * *